United States Patent
Da Rocha Pitta et al.

(10) Patent No.: US 8,217,068 B2
(45) Date of Patent: Jul. 10, 2012

(54) COMPOUND WITH ANESTHETICS ACTIVITY, METHODS FOR ITS PRODUCTION AND PHARMACEUTICAL COMPOSITIONS COMPRISING THE SAME

(75) Inventors: Ivan Da Rocha Pitta, Pernambuco (BR); Maria Do Carmo Alves De Lima, Pernambuco (BR); Teresinha Gonçalves da Silva, Pernambuco (BR); Gisele Zapata Sudo, Rio de Janeiro (BR); Suely Lins Galdino, Pernambuco (BR); Roberto Takashi Sudo, Pernambuco (BR)

(73) Assignees: Universidade Federal de Pernambuco—UFPE, Recife (BR); Universidade Federal do Rio de Janeiro—UFRJ, Rio de Janeiro (BR)

( * ) Notice: Subject to any disclaimer, the term of this patent is extended or adjusted under 35 U.S.C. 154(b) by 101 days.

(21) Appl. No.: 12/598,347

(22) PCT Filed: May 5, 2008

(86) PCT No.: PCT/BR2008/000145
§ 371 (c)(1),
(2), (4) Date: Oct. 30, 2009

(87) PCT Pub. No.: WO2008/134840
PCT Pub. Date: Nov. 13, 2008

(65) Prior Publication Data
US 2010/0130575 A1      May 27, 2010

(30) Foreign Application Priority Data
May 3, 2007   (BR) ...................... 0701016

(51) Int. Cl.
*A61K 31/4166* (2006.01)
*C07D 233/72* (2006.01)

(52) U.S. Cl. ..................................... 514/389; 548/317.1
(58) Field of Classification Search ............... 548/317.1; 514/389
See application file for complete search history.

(56) References Cited

U.S. PATENT DOCUMENTS
2,759,002 A * 8/1956 Close ...................... 548/317.1

FOREIGN PATENT DOCUMENTS
| | | |
|---|---|---|
| EP | 0545478 | 6/1993 |
| GB | 2386892 | 10/2003 |
| WO | 2004/010950 | 2/2004 |

* cited by examiner

*Primary Examiner* — Kamal Saeed
*Assistant Examiner* — Janet L Coppins
(74) *Attorney, Agent, or Firm* — Fildes & Outland, P.C.

(57) ABSTRACT

The present invention is related to a new series of chemical compounds, namely 3-benzyl-imidazolidine-2,4-dione substituted in the position 2 and/or 6 of benzyl ring by halogens as presented to the molecule named LPSF-PT-31, GIRSU-PAN and its therapeutic use as drug with analgesic, sedative and adjuvant of anesthetics activities. The invention is also related to a process for production of said compounds as well as pharmaceutical compositions comprising them.

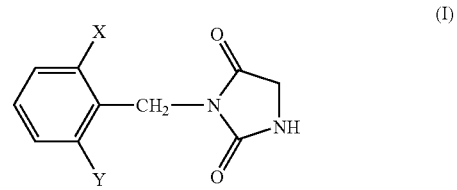

(I)

15 Claims, 3 Drawing Sheets

US 8,217,068 B2

COMPOUND WITH ANESTHETICS ACTIVITY, METHODS FOR ITS PRODUCTION AND PHARMACEUTICAL COMPOSITIONS COMPRISING THE SAME

FIELD OF THE INVENTION

The present invention is related to a new series of chemical compounds, namely 3-benzyl-imidazolidine-2,4-dione substituted in the position 2 and/or 6 of benzyl ring by halogens as presented to the molecule named LPSF-PT-31, GIRSUPAN and its therapeutic use as drug with analgesic, sedative and adjuvant of anesthetics activities.

The invention is also related to a process for production of said compounds as well as pharmaceutical compositions comprising them.

BACKGROUND OF THE ART

It is known that pain is pharmacologically treated by using non-steroidal anti-inflammatory drugs (NSAID), such as salicylates which mechanism of action is located in the peripheral sites, and the hypnotic-analgesics which action is focused in the central nervous system. The NSAIDs are a group of compounds widely used and well tolerate due to low incidence of severe side effects. The NSAID are very effective for regulating peripheral somatic pain, especially related to inflammatory processes. Due to the mechanism of action based on inhibition of ciclooxigenase enzymes type 1 (Nature New Biology, 2001, 231:232-235) and type 2 (PNAS, 1991, 88:2692-2696) the efficacy of NSAIDs for treatment of pains such as colic caused by obstruction, trauma, nerve compression or central nervous system pain, is limited. Few drugs are available for treatment of this modality of pain.

The pharmacological group recommended for the control of high intensity pain is the opioid, which the prototype compound is morphine, and even in this group few drugs are available. Clinical use of morphine and related drugs is not dissociated of several side effects as nausea, vomiting, itching and respiratory depression, which frequently interrupts the treatment. More recently, a therapeutic protocol to increase the potency of a drug based on association of an adjuvant compound with a main compound has been developed for treatment of patients with sustained pain. Thus, the adjuvant compound is directed to increase the efficacy and also the duration of the effect of drug like morphine for pain treatment. The main advantage of simultaneously use an adjuvant compound is the reduction of dose and frequency of administration of the main active drug, thus reducing side effects.

Besides the possibility to increase the analgesic effect of a drug such as morphine, an adjuvant compound also potentiates the intensity and duration of anesthesia induced by intrathecal administration of local anesthetics. This procedure is frequently recommended for abdominal lower surgery and for patients with chronic pain. One group of compounds that has been used for this purpose is the alpha-2 adrenoceptor agonists, such as clonidine. The efficacy of alpha-2 adrenoceptor agonists as analgesic is lower than the morphine, however, the ability for increasing the intensity and duration of analgesia of this drug in combination with other drugs is significant (Anesthesiology 1994, 80:837).

Other relevant pharmacological properties of alpha-2 adrenoceptor agonists are sedative and hypnotic effects (Anesthesiology 1988, 69:818-823). Although the efficacy as a hypnotic by itself is not as high as the barbiturates, alpha-2 adrenoceptor agonists are useful as pre-anesthetics drugs agent and as adjuvants for intravenous (Br. J. Anaesth. 1990, 65:157-163) and inhalation general anesthetics (Anesthesiology 1987, 67:11-19).

Hypotension is the main side effect related to the administration of alpha-2 adrenoceptor agonists due to their action in the important area of the brain that regulates the sympathetic nervous system outflow (Naunyn Schmiedebergs Arch Pharmacol., 1981, 317:120-125). This pharmacological effect for alpha-2 adrenoceptor agonists is known for several years even before the description of analgesic and sedative effect. For this reason, clonidine is classified as a hypertensive drug for therapy in classical pharmacological textbooks.

Due to the fact that alpha-2 adrenoceptors agonists used as adjuvants of analgesic and hypnotic compounds may cause decreasing of blood pressure, it is important to find new drugs with properties similar to clonidine but hemodynamically more stable.

Finding new prototype with central nervous system analgesic effect and adjuvant for anesthesia is clinically relevant due to limited number of drugs with these properties. Clonidine was one of the few drugs available (U.S. Pat. No. 4,094, 964), and, more recently the isomer of medetomidine, dexmedetomidine, is also available (U.S. Pat. No. 5,091,402) both with alpha-2 adrenoceptor agonist activity.

OBJECTIVES OF THE INVENTION

The present finding introduces a new series of compound with analgesic and sedative profile which effect results from activation of alpha-2 adrenoceptor demonstrated by complete reversion of the effect by the specific antagonist yohimbine. The analgesic activity can be demonstrated by both systemic and intrathecal administration of a preferred compound, LPSF-PT-31, GIRSUPAN. Part of the effect is also reversed by naloxone, a specific the antagonist of opioid receptor, however, the intensity of this effect is smaller when compared to the alpha-2 adrenoceptor.

Activity of the same molecule on more than one pharmacological target is revealed in several compounds due to similarity of arrangement of the macromolecule receptor and the dynamic of the molecules. The main advantage of LPSF-PT-31, GIRSUPAN, the compound found in this study in comparison to other compounds such as clonidine is the stability of blood pressure and heartbeat rate.

Therefore it is an objective of the invention a compound with anesthetics activity according to the formula (I) below:

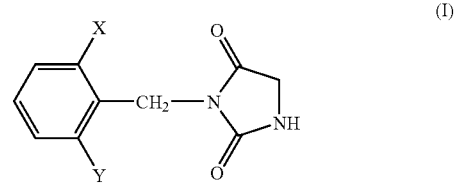

wherein X and Y are, each independently, selected from the group consisting of H, F, Cl, Br, I;

and pharmaceutically acceptable salts, solvates, hydrates and isomers thereof.

It is a further objective of the invention a process for production of anesthetics compounds comprising the step of reacting a benzyl chloride of formula (II):

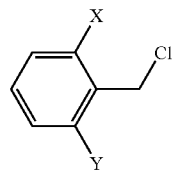

(II)

wherein X and Y are, each independently, selected from the group consisting of H, F, Cl, Br, I; with imidazolidine-2,4-dione.

It is a further objective of the invention a pharmaceutical composition comprising:
a) a compound with anesthetics activity according to the formula (I) below:

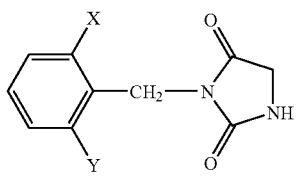

(I)

wherein X and Y are, each independently, selected from the group consisting of H, F, Cl, Br, I;
and pharmaceutically acceptable salts, solvates, hydrates and isomers thereof; and
b) a pharmaceutical acceptable carrier.

In a preferred embodiment, the pharmaceutical composition comprise an additional anesthetic, sedative and/or analgesic compound.

DETAILED DESCRIPTION OF THE INVENTION

Figure 1:
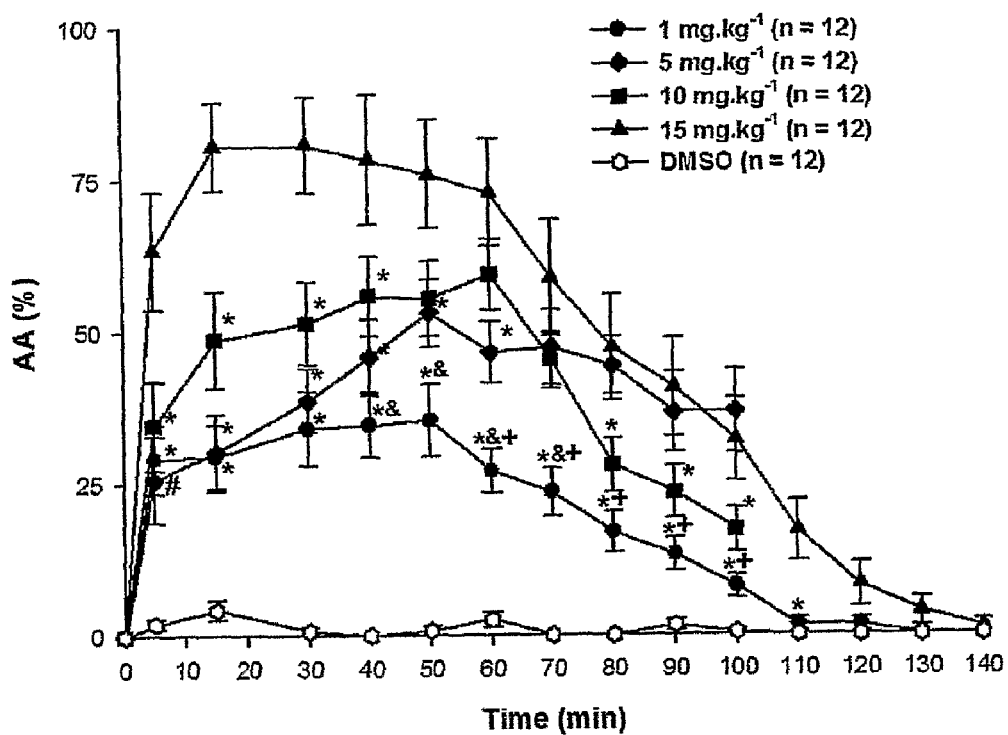
FIG. 1 shows the increase of % AA in a dose-dependent manner from LPSF-PT-31.

The following examples of the present invention are not to be considered as restrictive but rather illustrative of one of several ways to perform the invention.

The expression "pharmaceutically acceptable" should be understood as compounds, materials, compositions and/or dosage forms which are proper for use in humans and/or animals, without triggering any irritation, allergic or toxic response, or any other problem or complication, without any reasonable ratio between risk/benefit.

Anesthetics Compounds

The substances developed and prepared in this invention are characterized by having the ring imidazolidine-2,4-dione replaced in position 3 of this heterocyclic ring by a benzyl radical presenting the substituent X and Y in the ortho phenyl ring positions, according to the general formula (I):

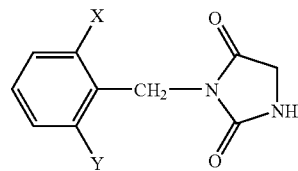

(I)

wherein X and Y are, each independently, selected from the group consisting of H, F, Cl, Br, I;
and pharmaceutically acceptable salts, solvates, hydrates and isomers thereof.

The expression "pharmaceutically acceptable salts" includes the compounds from the general formula (I) above which are modified by the addition of acids and/or bases. Examples include, without limitation, mineral or organic salts of basic residues such as amines, alkaline or organic salts or acid residues such as carboxylic acids.

The pharmaceutically acceptable salts include conventional non-toxic salts, such as quaternary ammonium salts, and derivatives from inorganic acids, such as hydrochloridric acid, bromidric acid, sulfuric acid, sulfamic acid, phosphoric acid, nitric acid; and organic acids such as acetic, propionic, succinic, glycolic, stearic, lactic, malic, tartaric, citric, ascorbic, maleic, hydroxymaleic, phenylacetic, glutamic, benzoic, salicylic, sulfanylic, sulphonic, oxalic, among others.

A preferred embodiment include the compound 3-(2-chloro-6-fluoro-benzyl)-imidazolidine-2,4-dione (LPSF-PT-31, GIRSUPAN) presenting the atoms of chlorine and fluorine in X and Y position, which leverage the activities found. Other suitable compounds include 3-(2,6-difluoro-benzyl)-imidazolidine-2,4-dione (LPSF-PT-122) and 3-(2,6-dichloro-benzyl)-imidazolidine-2,4-dione (LPSF-PT-123).

Process for Production

The process of production of the anesthetics of the present invention comprises the step of reacting a benzyl chloride of formula (II):

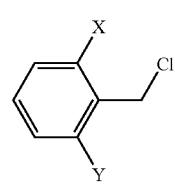

(II)

wherein X and Y are, each independently, selected from the group consisting of H, F, Cl, Br, I; with imidazolidine-2,4-dione.

In the experimental procedure of preparation of LPSF-PT-31 GIRSUPAN, LPSF-PT-122 and LPSF-PT-123, an equimolar mixture of imidazolidine-2,4-dione (C3H4N2O2 CAS 461-72-3) and 2-chloro-6-fluoro-benzyl chloride (C7H5CI2F CAS 127654-74-4) or 2,6-difluoro-benzyl chloride (C7H5CIF2 CAS 697-73-4) or 2,6-dichloro-benzyl chloride (C7H5CI3 CAS 2014-83-7) was dissolved in ethanol in the presence of a sufficient amount of sodium hydroxide needed in the formation of the sodium salt of imidazolidine-2,4-dione. The reaction mixture is heated and the formation of di-ortho substituted benzyl-imidazolidinediones is accompanied by thin layer chromatography.

At the end of the reaction the product formed is filtered and purified by crystallizations or column chromatography on silica in n-hexane:ethyl acetate 8:2 system. The LPSF-PT-31 presented a yield of 36% and a melting point of 155-156° C., the LPSF-PT-122 presented a yield of 32% and a melting point of 150-152° C. and LPSF-PT-123 presented a yield of 23% and a melting point of 160-1° C. The structural analysis of LPSF-PT-31, LPSF-PT-122 and LPSF-PT-123 synthesized was performed by the infrared spectra recorded at 66 Bruker IFS unit in tablet of KBr, the nuclear magnetic resonance spectra of proton made in a spectrophotometer device Bruker AC P 300, using the DMSO-$d_6$ as solvent and the mass spectra.

The spectroscopic features in the infrared, nuclear magnetic resonance of the protons and mass spectra of prepared compounds are in accordance with the structure. In mass spectrometry, the fragmentation observed and the intensity of the peaks of isotopes after electron impact are also in agreement with the proposed structures.

Pharmaceutical Composition

The compounds disclosed in the present invention are intended to be administered in a pharmaceutical composition comprising:

a) a compound with anesthetics activity according to the formula (I) below:

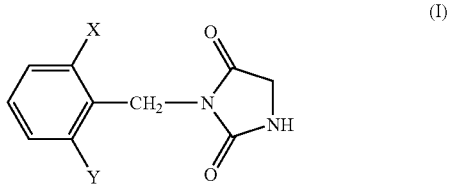

wherein X and Y are, each independently, selected from the group consisting of H, F, Cl, Br, I;

and pharmaceutically acceptable salts, solvates, hydrates and isomers thereof; and b) a pharmaceutical acceptable carrier.

In a preferred embodiment, the pharmaceutical composition comprises an additional active principle. The additional active principle has a synergistic effect with the compound of the present invention, so as to achieve the same level of sedation with a lower dose.

Suitable active principles include, without limitation, the anesthetics of the state of the art, such as morphine, codeine, sevoflurane, halothane, among others.

Pharmacological Evaluation

The in vivo tests performed in animals show that the compound LPSF-PT-31 GIRSUPAN has an analgesic and sedative activities and also potentiates the anesthetic activity.

The analgesic effect was demonstrated using a specific and validated method described as Hot Plate Test. The activity of several compounds with action in central nervous system as opioids, which the main drug is morphine, and the alpha-2 adrenoceptor agonist as clonidine have been identified by this method.

The analgesic activity of LPSF-PT-31, GIRSUPAN demonstrated in this invention was completely reversed by exposure of the animals to yohimbine a compound identified as antagonist of alpha-2 adrenoceptor (J Pharm Pharmacol 2005, 57).

The sedative activity of LPSF-PT-31, GIRSUPAN was demonstrated by measuring the motor activity of animals followed by an automated device. Decreasing of motor activity measured in this equipment suggest that the tested compound has a sedative effect. As described to the model of Hot Plate Test, the effect of LPSF-PT-31, GIRSUPAN in decreasing the motor activity was completely reversed by yohimbine sustaining the hypothesis that the target of this compound is the alpha-2 adrenoceptor.

The analgesic and sedative effects of LPSF-PT-31, GIRSUPAN probably are not related to the interaction with two different receptors because both effect were reversed by yohimbine. Thus, it seems that LPSF-PT-31, GIRSUPAN cause more than one effect after binding to the same alpha-2 adrenoceptor receptor. It is known that alpha-2 adrenoceptor is widely distributed in the peripheral organs, specially at the spinal cord which activation cause regulation of pain mechanism and also, in the central nervous system in the locus coerulus regulating the sedative-hypnose effects (Anesthesiology 1992, 76:948).

Example 1

Investigation of Central Nervous System Analgesic Activity

The analgesic activity of LPSF-PT-31, GIRSUPAN was investigated in male Swiss mice weighting 18-24 grams using the Hot Plate Test method (Brain Res. 1983, 245-252). The animals were positioned on a hot plate stabilized at 52° C. using the equipment Analgesic Meter-Letica LE 7406. When the pain threshold was achieved the animals raised and licked the front paw to cool down the temperature. The time between positioning the animals on the plate and lick the paw was the latency of the pain reaction. The maximal time (cut-off) allowed to the animals staying on the hot plate was three times the latency time measured on the control. The cut-off was very important to avoid skin damage of the paw.

The analgesic effect of the tested compounds was converted to a unit denominated analgesic activity (% AA) (Brain Res. 1983, 245-252) calculated by equation $\% AA = ((\text{post-drug latency}) - (\text{control latency}))/((\text{cut off}) - (\text{control latency})) \times 100$. The experimental protocol used to test the analgesic effect of the compound LPSF-PT-31, GIRSUPAN, consisted to measure the AA in the control condition (before drug administration) and after (i.p.) intraperitoneal administration of increasing dose (1, 5, 10 and 15 mg·kg$^{-1}$).

In another experimental group, dimethyl sulfoxide used as vehicle for diluting LPSF-PT-31, GIRSUPAN, was i.p. administered at same volume used for the tested drug. The AA was measured until complete recovery to the control condition.

Figure 2:
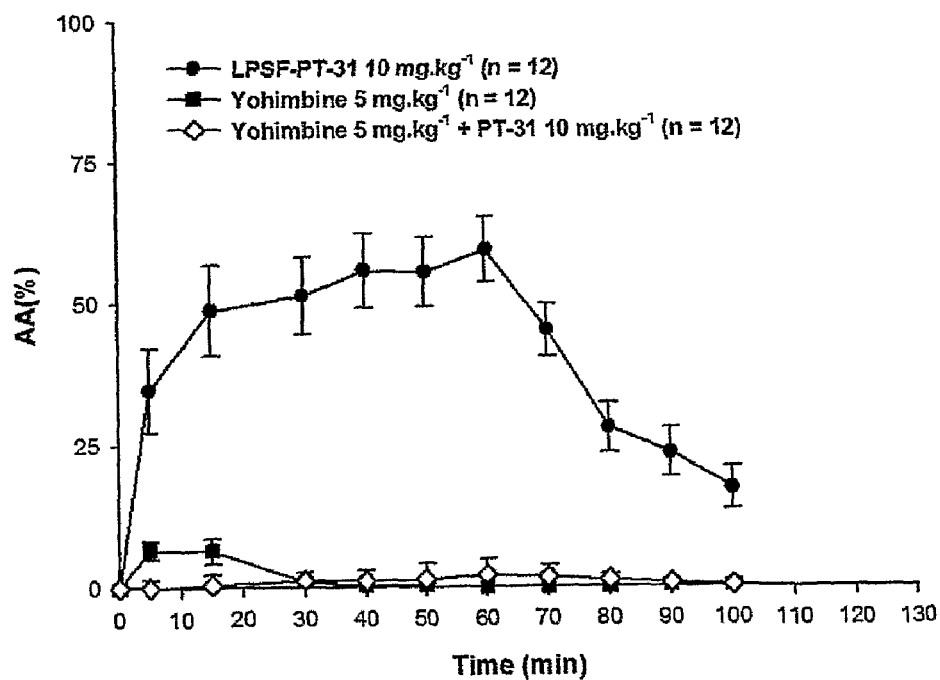
FIG. 2 shows the reversion of anestethic activity of LPSF-PT-31 by yohimbine.

The results shown in the FIG. 1 demonstrate that LPSF-PT-31, GIRSUPAN increased the % AA in a dose-dependent manner. The maximal effect observed with dose of 15 mg·kg$^{-1}$ was about 80% AA. The peak of analgesic effect occurred at approximately 20 min suggesting a quick absorption of LPSF-PT-31, GIRSUPAN. The plateau of effect was sustained for 40-50 min and then began to decay until a complete recovery from the analgesic effect at about 100-120 min. The analgesic effect of LPSF-PT-31, GIRSUPAN after i.p. administration was not reversed by previous treatment with flumazenil (0.3 mg·kg$^{-1}$) an antagonist of benzodiazepine receptor and partially reversed by naloxone (1 mg·kg$^{-1}$ i.p.) an antagonist of opioid receptor. However, administration of yohimbine (5 mg·kg$^{-1}$, i.p.) completely reversed effect of LPSF-PT-31, GIRSUPAN (10 mg·kg$^{-1}$) strongly suggesting that analgesic effect involves action of alpha-2 adrenoceptor (FIG. 2).

Figure 3:
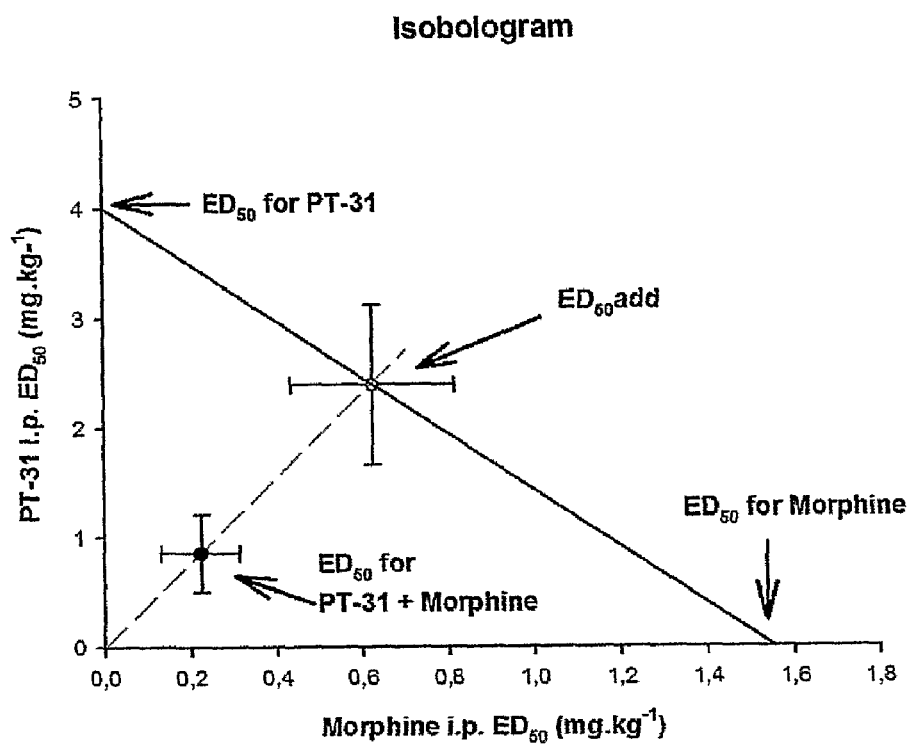
FIG. 3 shows the isobologram for LPSF-PT-31 and morphine

The adjuvant of analgesic effect of LPSF-PT-31, GIRSUPAN was investigated in a protocol, which the main elected analgesic compound was morphine. First, we determined the dose of morphine that cause 50% of maximal analgesic effect (DE50) after administration (i.p.) in incremental doses. Then, DE50 for the analgesic effect of LPSF-PT-31, GIRSUPAN was also calculated. Fraction of association of DE50 of each drug was administrated and the DE50 of combination was determined. A isobolographic analysis (FIG. 3) using the DE50 of each drug and of the combination was performed using a computer program (*Life Sci* 1989 45: 947-961) to determine the type of interaction. This analysis shows strong synergic interaction between LPSF-PT-31, GIRSUPAN and morphine. It means the LPSF-PT-31, GIRSUPAN is a new compound potentially able to reduce the dose and frequency of administration of morphine for treatment of severe and chronic pain.

Example 2

Investigation of Analgesic Effect after Intrathecal Administration

Stimulation of alpha-2 adrenoceptors distributed at spinal cord cause analgesia. Previous results suggested that systemic administration of LPSF-PT-31, GIRSUPAN stimulated this class of receptor. Thus, the analgesic activity of LPSF-PT-31, GIRSUPAN was investigated after intrathecal administration. Wistar male rats weighting 240-280 grams were positioned in abdominal under light general anesthesia with sevoflurane. Puncture between L4-L5 was performed with low diameter needle (29 G) and LPSF-PT-31, GIRSUPAN was injected at dose of 20, 40, 80 or 160 µg diluted in constant volume of 50 µl. Sevoflurane was the elected anesthetic due to low blood solubility causing a fast induction and recovery of anesthesia.

Figure 4:
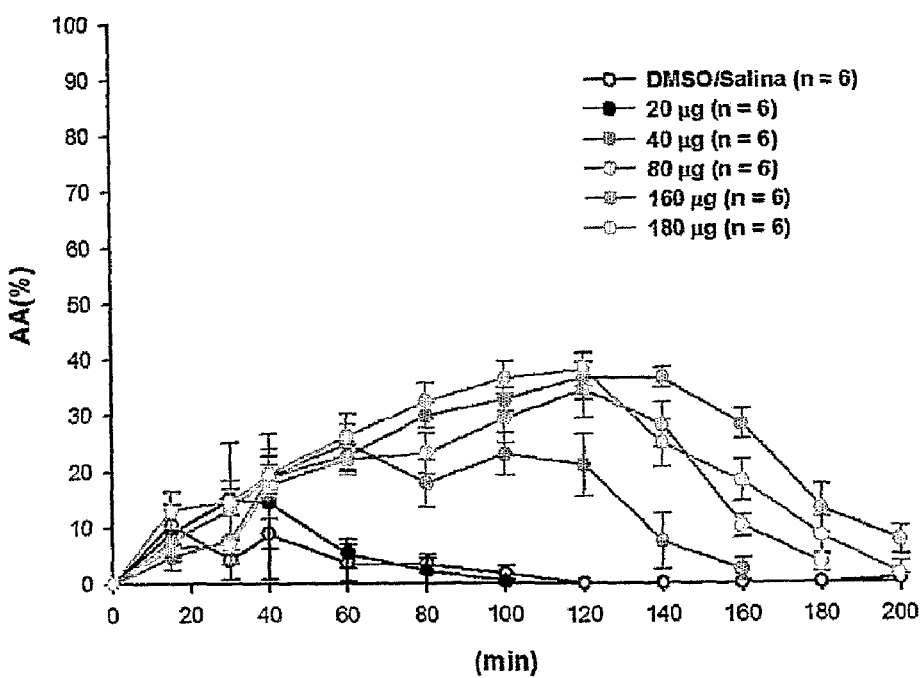
FIG. 4 shows the reduction of pain reaction after intrathecal administration in a dose-dependent manner.

Thus, the animals were completely recovered few minutes after punction and injection LPSF-PT-31, GIRSUPAN and AA activity started to measure from 10 minutes. As shown in the FIG. 4 LPSF-PT-31, GIRSUPAN reduces the pain reaction after intrathecal administration in a dose-dependent manner. The maximal analgesic effect measured by Hot Plate was ca. 40% sustained by 180 minutes. This intensity of analgesic effect is observed with alpha-2 adrenoceptor agonist as clonidine. This experimental protocol demonstrated that LPSF-PT-31, GIRSUPAN cause analgesic effect after intrathecal administration suggestion a activation of alpha-2 adrenoceptor.

Example 3

Investigation of Sedative Activity

The sedative activity of 3-(2-chloro-6-fluoro-benzyl)-imidazolidine-2,4-dione LPSF-PT-31, GIRSUPAN was investigated in male Swiss mice weighting 18-24 grams by measuring the motor activity (Motor Activity Monitor, Letica LE 8811). In this equipment the animals are positioned in an open square field and a set of invisible beans cross the field. The interruption of the beans was used to quantify the motor activity. After a period of adaptation the motor activity of the animals was measured during 20 min.

Figure 5:
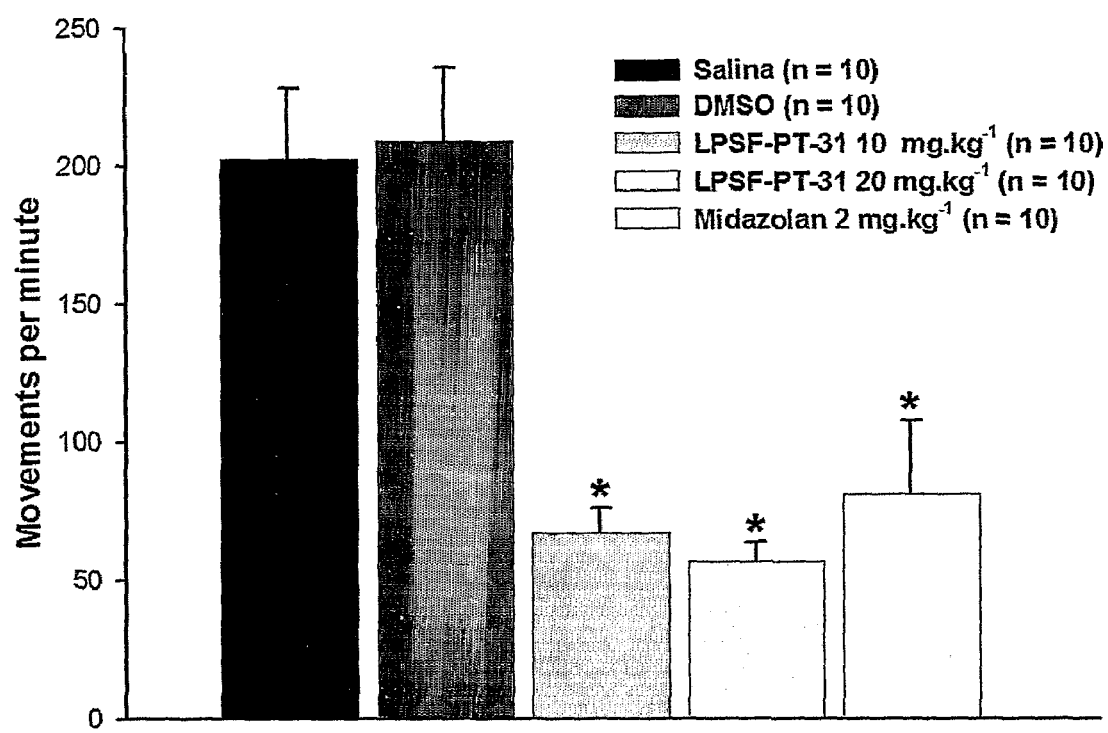
FIG. 5 shows the reduction of motor activity caused by LPSF-PT-31, GIRSUPANI.

Decrease of motor activity represents reduction of brain activity and this observation is useful to investigate the effect of drug with sedative, hipnotic, anxyolitic and general anesthetic properties (Bioorg. Med. Chem. 2006, 14:632-640). Thus, measurement of motor activity is not a method to identify a specific group of pharmacological class. The treatment of animals with LPSF-PT-31, GIRSUPAN (10 mg·kg$^{-1}$) reduced the motor activity of ca. 80% and the intensity of this effect was comparable to midazolam drug used as positive control FIG. 5.

Example 4

Investigation of Activity on Cardiovascular System

Hypotension and reduction of heart rate are the major concern of alpha-2 adrenoceptor agonist as clonidine. These effects are justified by decreasing the central nervous system sympathetic outflow due to activation of alpha-2 adrenoceptor. With the aim to investigate if LPSF-PT-31, GIRSUPAN could cross the brain barrier and reduces the hemodynamic response, Wistar male rats weighing 230-280 grams were prepared for blood pressure and electrocardiogram (EKG) recording. The heart rate was estimated by analysis of EKG. LPSF-PT-31, GIRSUPAN (10 mg/kg) was injected trough external jugular vein in a single dose in awaked animals. The blood pressure and the heart rate were not changed showing that LPSF-PT-31, GIRSUPAN is a stable compound for the cardiovascular system differently that occurs with clonidine.

The invention claimed is:

1. Compound with anesthetic activity characterized by the general formula (I):

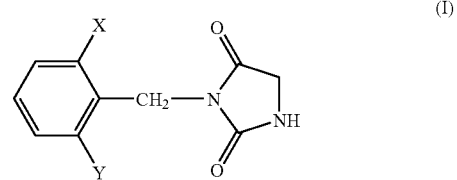

(I)

wherein one of X and Y is selected from the group consisting of F, Cl, Br, and I, and the other of X and Y is selected from the group consisting of H, F, Cl, Br, and I;

and pharmaceutically acceptable salts and isomers thereof.

2. Compound, according to claim 1, characterized by the fact that X is F and Y is Cl.

3. Compound, according to claim 1, characterized by the fact that X is Cl and Y is Cl.

4. Compound, according to claim 1, characterized by the fact that X is F and Y is F.

5. Process for production of a compound with anesthetic activity characterized by comprising the step of reacting a benzyl chloride of formula (II):

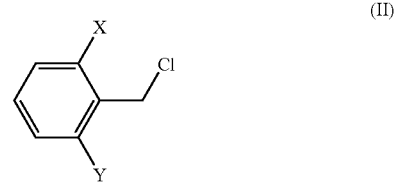

(II)

wherein one of X and Y is selected from the group consisting of F, Cl, Br, and I, and the other of X and Y is selected from the group consisting of H, F, Cl, Br, and I; with imidazolidine-2,4-dione.

6. Process, according to claim 5, characterized by the fact that X is F and Y is Cl.

7. Process, according to claim 5, characterized by the fact that X is Cl and Y is Cl.

8. Process, according to claim 5, characterized by the fact that X is F and Y is F.

9. Process, according to claim 5, characterized by the fact that the benzyl chloride and the imidazolidine-2,4-dione are mixed in ethanol.

10. Process, according to claim 9, characterized by the fact that NaOH is added to the mixture.

11. Process, according to claim 5, characterized by comprising a further step of heating the mixture.

12. Pharmaceutical composition characterized by the fact that it comprises:

(a) a compound with anesthetics activity according to the formula (I) below:

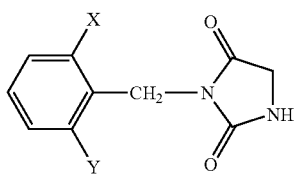

wherein one of X and Y is selected from the group consisting of F, Cl, Br, and I, and the other of X and Y is selected from the group consisting of H, F, Cl, Br, and I;

and pharmaceutically acceptable salts and isomers thereof; and (b) a pharmaceutical acceptable carrier.

13. Pharmaceutical composition, according to claim 12, characterized by the fact that X is F and Y is Cl.

14. Pharmaceutical composition, according to claim 12, characterized by the fact that X is Cl and Y is Cl.

15. Pharmaceutical composition, according to claim 12, characterized by the fact that X is F and Y is F.

* * * * *